US006150175A

United States Patent [19]

Shelton et al.

[11] Patent Number: 6,150,175

[45] Date of Patent: Nov. 21, 2000

[54] COPPER CONTAMINATION CONTROL OF IN-LINE PROBE INSTRUMENTS

[75] Inventors: Gail D. Shelton; Gayle W. Miller, both of Colorado Springs, Colo.

[73] Assignee: LSI Logic Corporation, Milpitas, Calif.

[21] Appl. No.: 09/212,366

[22] Filed: Dec. 15, 1998

[51] Int. Cl.[7] .......................... G01N 33/00; G01N 33/20; B08B 7/00

[52] U.S. Cl. .................................... 436/80; 436/49; 134/6

[58] Field of Search .................................. 134/6; 436/80, 436/49

[56] References Cited

U.S. PATENT DOCUMENTS

| | | | |
|---|---|---|---|
| 4,314,855 | 2/1982 | Chang et al. | 134/6 |
| 4,368,220 | 1/1983 | Eldridge et al. | 427/255.4 |
| 4,922,205 | 5/1990 | Shimizu et al. | 324/454 |
| 5,225,037 | 7/1993 | Elder et al. | 156/644 |
| 5,280,236 | 1/1994 | Takahashi et al. | 324/158 |
| 5,447,763 | 9/1995 | Gehlke | 428/34.1 |
| 5,527,707 | 6/1996 | Fukazawa | 436/72 |
| 5,530,278 | 6/1996 | Jedicka et al. | 257/432 |
| 5,686,314 | 11/1997 | Miyazaki | 436/80 |
| 5,778,485 | 7/1998 | Sano et al. | 15/301 |
| 5,868,863 | 2/1999 | Hymes et al. | 134/6 |
| 5,968,282 | 10/1999 | Yamasaka | 134/6 |
| 5,994,142 | 11/1999 | Yamasaki et al. | 436/80 |
| 6,037,182 | 3/2000 | Weems | 436/80 |

*Primary Examiner*—Randy Gulakowski
*Assistant Examiner*—Saeed Chaudhry

[57] ABSTRACT

Radio frequency photo conductive decay is used to monitor a small piece of high-grade silicon to determine if copper contamination has been removed from a probe tool. A probe tool is placed in contact with a small "waferette" of silicon repeatedly until the copper signal is diminished, indicating that the tool may be used for other products without concern for copper contamination.

28 Claims, 2 Drawing Sheets

COPPER CONTAMINATION CONTROL OF IN-LINE PROBE INSTRUMENTS

BACKGROUND OF THE INVENTION

1. Technical Field

The present invention relates to a method and apparatus for copper contamination control on in-line probe instruments typically used in integrated circuit fabrication and like processes.

2. Description of Related Art

A present trend in the integrated circuit fabrication industry is a move away from aluminum and towards copper damascene interconnect processes. A collateral problem raised by the increased use of copper in such applications is the potential for copper contamination during various phases of the chip fabrication in light of copper's diffusivity in silicon. If copper contamination finds its way to the active areas of the silicon on an integrated circuit package, the silicon can easily lose its critical effective properties, such as design capacitance at a specific contaminated site.

The potential for copper contamination raises a host of technical and logistical issue for an integrated circuit fabricator. For example, many metrology tools are used throughout the fabrication process. Typically, the availability of these metrology tools creates a bottleneck at the testing steps of the fabrication process. As integrated circuit fabricators transition from aluminum to copper technologies, cost considerations may require that the metrology tools used for the aluminum processes are also used for the copper processes. Yet, some of these tools require physical contact on a chip's metal layer during testing, resulting in residual metal contamination remaining on the tool after the test is complete. For example, electrical probe tips shows signs of copper contamination after being used on a copper wafer. This phenomena raises a concern of cross-contamination between sample pieces of copper to the substrate.

Accordingly, a need exists for copper contamination control on typical in-line probe instruments. The contamination control should include a method for quickly removing any copper contamination from the tip of the in-line probe instrument and further confirming the decontamination of the probe tip prior to continued testing.

SUMMARY OF THE INVENTION

A process and apparatus for copper contamination control on in-line instruments is provided in which the probe tip is placed in contact several times with an absorbent material, such as silicon, in order to clean the probe tip. The invention uses this removal mechanism while monitoring copper contamination of a small "waferette" of high-grade silicon as it makes a series of contacts with the probe tip. When the probe contacts the wafer without leaving a trace of copper, the probe tip is clean for contact with any layer in the process, or with the wafer on an aluminum-copper route. The waferette of high-grade silicon is monitored by means of radio frequency photo conductive decay (RF-PCD) in order to determine that the probe tip is no longer depositing copper on the waferette.

The above, as well as additional features and advantages of the present invention will become apparent in the following written detailed description.

DESCRIPTION OF THE DRAWINGS

The novel features believed characteristic of the invention are set forth in the appended claims. The invention itself, however, as well as a preferred mode of use, further objectives and advantages thereof, will be best understood by reference to the following detailed description of illustrative embodiments when read in conjunction with the accompanying drawings, wherein:

DETAILED DESCRIPTION

Figure 1:
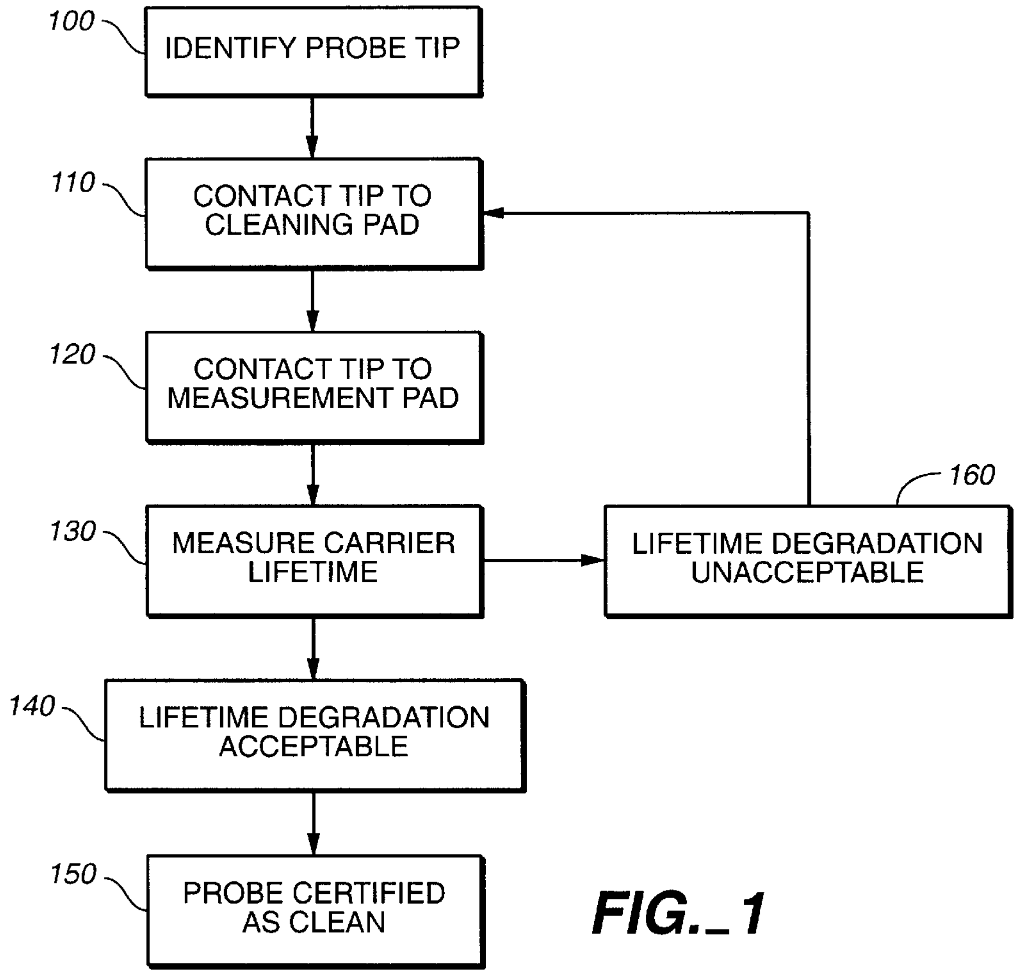
FIG. 1 is a flow chart illustrating the overall method of the invention.

FIG. 1 is a flow chart illustrating the overall method of the invention. The first step involves identifying the probe tip to be cleaned and tested (Step 100). This might involve identifying a tool probe tip that has been used in physical contact with metal layers during chip testing or which has not been confirmed to be free of copper contamination prior to use in a testing application. The probe tip identified could be a component of any number of metrology tools used in the integrated circuit fabrication process, such as test probes manufactured by Keithley or test probes manufactured by Electroglass.

The next step in the method involves placing the probe tip in physical contact with a cleaning pad (step 110). This cleaning pad is comprised of any material that demonstrates the ability to remove copper contamination from the tip of the probe tool. For example, it has been demonstrated that a wafer of silicon will remove copper contamination from the tip of metrology probe tool if the tip is repeatedly touched on the wafer. Other materials, such as soft metals (for example aluminum), can also be used for the cleaning pad material. The probe tip should be placed in physical contact with the cleaning pad repeatedly in quick succession (for example, tapping the tip on the pad four to five times over a period of several seconds) to ensure that the copper contamination is transferred from the probe tip to the cleaning pad.

In one embodiment of the invention, the probe tip is next placed into contact with a measurement pad or "waferette" of silicon (step 120). The best results are achieved when using a silicon waferette of high purity which is clean from any copper contamination residue. The minority carrier lifetime is then measured on the measurement silicon (step 130) (a process that will be described further below) to determine if the previous contact step 120 deposited any copper contamination on the measurement silicon. If the lifetime degradation is measured at an acceptable level (step 140) (for example, less than 2%), then the test has confirmed that the probe tip no longer deposits any copper contamination when placed into contact with clean silicon and, therefore, can be certified as clean and relatively free of copper contamination (step 150).

If during the carrier lifetime measurement in step 130, the carrier lifetime degradation is designated not acceptable (step 160), this is an indication that copper contamination was transferred from the probe tip to the measurement silicon during the last contact step 120. Consequently, the probe tip would again require repeated contact with a cleaning pad in step 110 before the tip could be placed in contact with silicon measurement pad in step 120 a second time. This cycle is repeated until the measured carrier lifetime degradation is recorded at an acceptable level in step 140.

The method illustrated in FIG. 1 requires the use of a separate cleaning pad contact step 110 and a measurement pad contact step 120. For example, a low-grade silicon wafer could be used during the cleaning pad step 110, and a high-grade silicon waferette used for the measurement pad step 120. In an alternative embodiment, however, a single pad of, for example, silicon, could be used in both the cleaning pad step 110 and measurement pad step 120. In such case, the carrier lifetime measurement step 130 would be directed towards the relative change in carrier lifetime registered between the previous measurement made on the silicon wafer. If the relative change measured is an acceptable level, the probe can be certified as clean. Otherwise, the cleaning step 110 is repeated.

Figure 2:
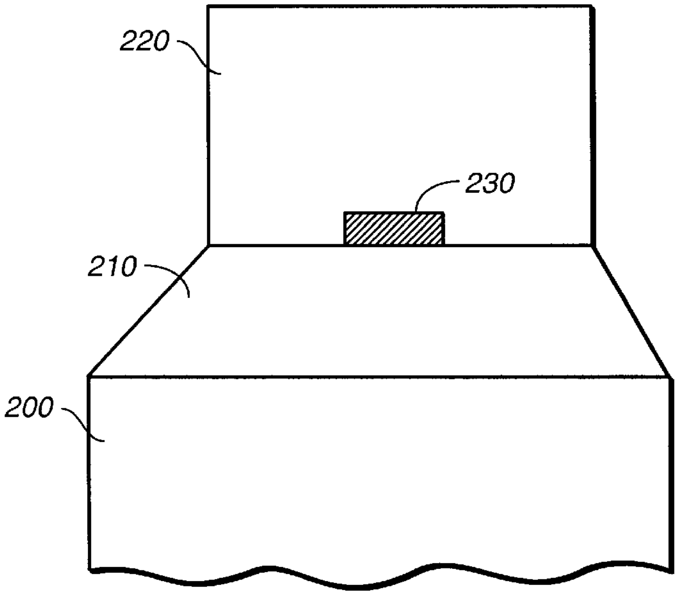
FIG. 2 illustrates a frontal view of a typical probe station incorporating the invention; and, FIG. 3 illustrates a schematic of the measurement hardware of the invention.

FIG. 2 illustrates a frontal view of a probe station 200 incorporating the measurement hardware used to test the measurement pad for copper residue. The probe station 200 is shown as a typical laboratory workstation with a work counter 210 and a headboard 220. The probe station 200 is tooled such that the measurement hardware 230 (which will be explained in further detail below in conjunction with FIG. 3) is situated in the headboard 220 and is more or less flush with the work surface 210.

Figure 3:
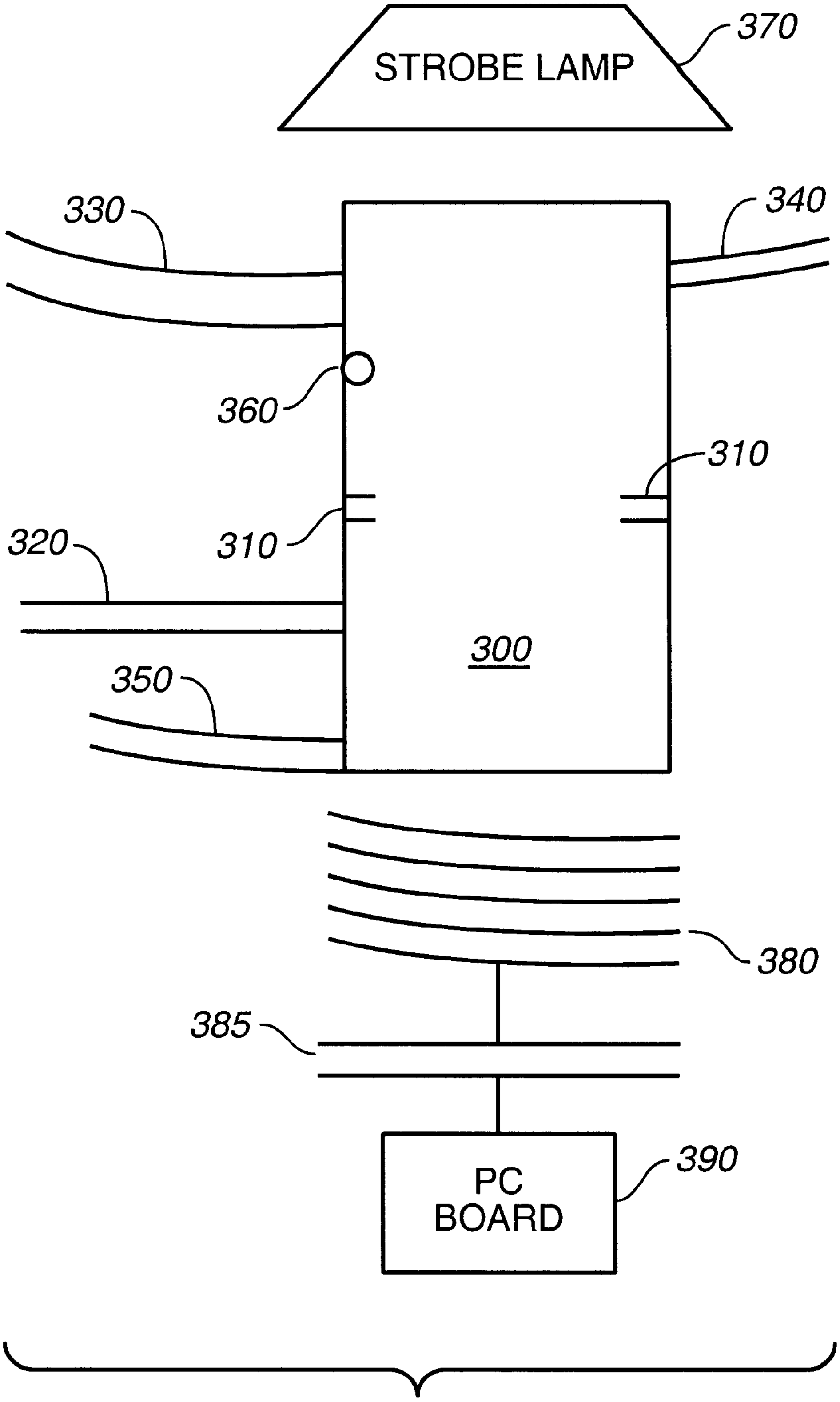

FIG. 3 is a schematic illustration of the measurement hardware of the invention. The hardware consists of a vessel or reservoir 300 manufactured with a slot 310 for holding the silicon waferette (not shown). The reservoir 300 volume can be relatively small, for example a total volume of approximately 200 ml. The detection of copper residue on the waferette is measured most efficiently in a dilute hydrogen fluoride median, which is introduced into the reservoir 300 via the median fill line 330. The hydrogen fluoride median should be non-aerated by, for example, sparging of the medium with argon by way of an argon sparge line 320. FIG. 3 also shows a de-ionized water line 340 used for flushing the vessel and waferette after testing is complete. Fluids in the vessel are drained by way of an acid drain 350, and fluid levels are measured by a level sensor 360.

The waferette (not shown) that is inserted into slot 310 can be fashioned the size and shape of a glass slide and articulate with the sample median by means of transport mechanism (robotics, belts, etc.). All of the illustrated lines, 320, 333, 340, 350 are preferably soft-plumbed to allow the reservoir some range of motion, if necessary, to articulate with the transport mechanism.

The density of the recombination centers on the waferette determines the decay time which can be monitored using the apparatus shown by virtue of radio frequency photo conductive decay (RF-PCD) technique. A small strobe lamp 370 is positioned above the sample medium to provide for the injection of excess carriers to the waferette substrate. This strobe lamp 370 energizes the surface of the waferette, thus providing a measurable means, decay time, of determining whether a copper deposit can be found on the waferette. A radio frequency (RF) coil 380 monitors the wafer conductivity, communicating by way of an interface 385 with a computer board 390, which performs the logic steps necessary to relate the test results to the operator.

The invention has been disclosed in an embodiment relating to removing copper contamination from a probe tip using silicon as an absorbent cleaning material. However, the invention could include similar embodiments for removing other contaminates, such as other metal compounds, from probe tips using silicon or other absorbent materials by following the same general processing steps or using the same general apparatus disclosed.

While the invention has been particularly shown and described with reference to preferred embodiments, it will be understood by those skilled in the art that various changes in form and detail may be made therein without departing from the spirit and scope of the invention.

What is claimed is:

1. A method for testing for copper contamination on a probe instrument having a tip comprising the steps of:

(a) touching the tip of said probe instrument on a cleaning pad suitable for removing copper contamination from said tip; and (b) testing the cleaning pad to determine if any copper contamination has been removed from said tip.

2. The method of claim 1 wherein the cleaning pad of step (a) is comprised of silicon.

3. The method of claim 1 wherein the cleaning pad of step (a) is comprised of a soft metal.

4. The method of claim 1 wherein the cleaning pad of step (a) is comprised of aluminum.

5. The method of claim 1 wherein the testing of step (b) comprises monitoring the cleaning pad using radio frequency photo conductive decay.

6. The method of claim 5 wherein the cleaning pad is monitored in a liquid acid medium.

7. The method of claim 5 wherein the cleaning pad is monitored in a liquid hydrogen fluoride medium.

8. A method for testing for contamination on a probe instrument having a tip comprising the steps of:

(a) bringing the tip of said probe instrument into temporary physical contact with a cleaning pad;

(b) bringing the tip of said probe instrument into temporary physical contact with a measurement pad; and (c) testing the measurement pad to determine if any contamination has been removed from said tip.

9. The method of claim 9 wherein the cleaning pad of step (a) is comprised of silicon.

10. The method of claim 9 wherein the cleaning pad of step (a) is comprised of a soft metal.

11. The method of claim 8 wherein the cleaning pad of step (a) is comprised of aluminum.

12. The method of claim 8 wherein the measurement pad of step (b) is comprised of silicon.

13. The method of claim 8 wherein the measurement pad of step (b) is comprised of high-grade silicon.

14. The method of claim 8 wherein the testing of step (c) comprises monitoring the cleaning pad using radio frequency photo conductive decay.

15. The method of claim 14 wherein the measurement pad is tested in a liquid acid medium.

16. The method of claim 14 wherein the measurement pad is tested in a liquid hydrogen fluoride medium.

17. A method for testing for copper contamination on a probe instrument having a tip comprising the steps of:

(a) touching the tip of said probe instrument on a cleaning pad suitable for removing copper contamination from said tip;

(b) touching the tip of said probe instrument on a measurement pad suitable for removing copper contamination from said tip;

(c) placing said measurement pad in a liquid medium;

(d) energizing said measurement pad; and (e) monitoring the measurement pad's conductivity to determine the presence of copper on the measurement pad.

18. The method of claim 17 wherein the cleaning pad of step (a) is comprised of silicon.

19. The method of claim 17 wherein the cleaning pad of step (a) is comprised of a soft metal.

20. The method of claim 17 wherein the cleaning pad of step (a) is comprised of aluminum.

21. The method of claim 17 wherein the measurement pad of step (b) is comprised of silicon.

22. The method of claim 17 wherein the measurement pad of step (b) is comprised of high-grade silicon.

23. The method of claim 17 wherein the medium of step (c) comprises an acid.

24. The method of claim 17 wherein the medium of step (c) comprises hydrogen fluoride.

25. The method of claim 23 wherein the acid is dilute and is non-aerated.

26. The method of claim 25 wherein the acid is non-aerated by sparging with argon.

27. The method of claim 17 wherein the energizing of step (d) comprises use of a strobe lamp.

28. The method of claim 17 wherein the monitoring of step (e) comprises use of a radio frequency coil communicating with a computer board.

* * * * *